US012601751B2

(12) United States Patent
    Cao

(10) Patent No.: US 12,601,751 B2
(45) Date of Patent: Apr. 14, 2026

(54) PROTEIN ANTIGEN COMBINATION FOR DETECTION OF ALZHEIMER'S DISEASE AND APPLICATION THEREOF

(71) Applicant: Shanghai Zhongqi Biotechnology Co., Ltd., Shanghai (CN)

(72) Inventor: Liqin Cao, Shanghai (CN)

(73) Assignee: Shanghai Zhongqi Biotechnology Co., Ltd., Shanghai (CN)

( * ) Notice: Subject to any disclaimer, the term of this patent is extended or adjusted under 35 U.S.C. 154(b) by 0 days.

(21) Appl. No.: 18/996,523

(22) PCT Filed: Sep. 26, 2024

(86) PCT No.: PCT/CN2024/121352
    § 371 (c)(1),
    (2) Date: Jan. 17, 2025

(87) PCT Pub. No.: WO2025/148411
    PCT Pub. Date: Jul. 17, 2025

(65) Prior Publication Data
    US 2025/0258184 A1     Aug. 14, 2025

(30) Foreign Application Priority Data
    Jan. 9, 2024    (CN) .......................... 202410026086.9

(51) Int. Cl.
    *G01N 33/68*         (2006.01)
(52) U.S. Cl.
    CPC ..... *G01N 33/6896* (2013.01); *G01N 33/6875* (2013.01); *G01N 2800/2821* (2013.01)
(58) Field of Classification Search
    CPC ........... G01N 33/6896; G01N 33/6875; G01N 2800/2821; G01N 2333/47; G01N 2333/978; G01N 33/573; G01N 2333/90245
    See application file for complete search history.

(56) References Cited

U.S. PATENT DOCUMENTS

| | | |
|---|---|---|
| 2013/0157888 A1 | 6/2013 | Nagele et al. |
| 2014/0304845 A1 | 10/2014 | Loboda et al. |
| 2014/0315736 A1 | 10/2014 | Nagele et al. |
| 2016/0289762 A1 | 10/2016 | Koh et al. |
| 2017/0219611 A1 | 8/2017 | Ward et al. |
| 2021/0396769 A1 | 12/2021 | Shen et al. |
| 2023/0102038 A1 | 3/2023 | Anand et al. |
| 2023/0176075 A1 | 6/2023 | Guo et al. |

FOREIGN PATENT DOCUMENTS

| | | |
|---|---|---|
| CN | 1440423 A | 9/2003 |
| CN | 1928557 A | 3/2007 |
| CN | 101041071 A | 9/2007 |
| CN | 105163726 A | 12/2015 |
| CN | 111426850 A | 7/2020 |
| CN | 111471095 A | 7/2020 |
| CN | 111793627 A | 10/2020 |
| CN | 112062826 A | 12/2020 |
| CN | 112272516 A | 1/2021 |
| CN | 117538545 A | 2/2024 |

OTHER PUBLICATIONS

International Search Report and Written Opinion of PCT/CN2024/121352, mailed Jan. 10, 2025, including translations, 25 pages.
Mammalian Gene Collection Progam Team, "Generation and initial analysis of more than 15,000 full-length human and mouse cDNA sequences", Proc. Natl. Acad. Sci. USA, vol. 99, Issue 26, 2002, 16899-16903, 5 pages.
Genbank Accession No. AAC35352.1. SPF31 [*Homo sapiens*]. National Library of Medicine, Sep. 14, 1998. [online] [retrieved on Oct. 7, 2025] Retrieved from the Internet <URL: https://www.ncbi.nlm.nih.gov/protein/AAC35352.1?report=genbank&log $=protalign&blast_rank=3&RID=S0UWMC1M01>. 2 pages.
GENBANK Accession No. AAH63436.1. DOC2A protein [*Homo sapiens*]. National Library of Medicine, Dec. 12, 2003 [online] [retrieved on Oct. 7, 2025] Retrieved from the Internet <URL: https://www.ncbi.nlm.nih.gov/protein/AAH63436.1?report=genbank&log$=protalign&blast_rank=4&RID=S0SXVGZ0013>. 3 pages.

*Primary Examiner* — Olga N Chernyshev
(74) *Attorney, Agent, or Firm* — LEASON ELLIS LLP

(57) ABSTRACT

The present disclosure belongs to the field of biological detection, and particularly relates to a protein antigen combination for detection of Alzheimer's disease (AD) and application thereof. The specific technical solution is as follows: An antigen combination is provided, wherein the antigen combination at least simultaneously includes the following proteins: DOC2A, LGALS1, KDM4D, and ADARB1. The present disclosure provides several new protein antigens and the combination thereof, which can be used for early-screening detection or diagnosis of AD, and are particularly suitable for risk assessment and prediction prior to the onset of AD. Meanwhile, the protein antigens and the combination thereof can distinguish AD from other types of dementia, and can be further prepared into related reagents or kits according to needs.

4 Claims, No Drawings
Specification includes a Sequence Listing.

PROTEIN ANTIGEN COMBINATION FOR DETECTION OF ALZHEIMER'S DISEASE AND APPLICATION THEREOF

INCORPORATION-BY-REFERENCE OF SEQUENCE LISTING

The application contains a sequence listing which has been submitted electronically in XML format and is hereby incorporated by reference in its entirety. Said XML copy, created on Feb. 12, 2025, is named 11540_013019-US0_SL-v2.xml and is 13615 bytes in size.

TECHNICAL FIELD

The present disclosure belongs to the field of biological detection, and particularly relates to a protein antigen combination for early detection of Alzheimer's disease and application thereof.

BACKGROUND ART

Alzheimer's disease (AD) is one of the most prevalent forms of dementia diseases, accounting for 60% to 80% of all dementia cases. AD is generally classified into preclinical, mild cognitive impairment (MCI), mild (early), moderate (mid), and severe (late) depending on patients' conditions. Preclinical (including an AD-derived subjective cognitive decline stage) and MCI stages are identified as extremely early stages of AD. At the preclinical and MCI stages, patients often exhibit less obvious symptoms, while abnormalities in biomarker indexes have already emerged. Should the timely and accurate diagnosis be feasible during the early stage without (obvious) symptoms, the therapeutic intervention for patients could be initiated a decade or two decades prior to the onset.

In 2023, the Alzheimer's Association International Conference (AAIC) announced *National Institute on Aging-Alzheimer's Association (NIA-AA) Revised Clinical Criteria for Alzheimer's Disease (draft)*. The draft has classified biomarkers into three major categories, respectively: blood based biomarkers (BBBM), cerebrospinal fluid (CSF) biomarkers and "Golden standard" imaging (positron emission tomography/magnetic resonance imaging (PET/MRI)) biomarkers.

The CSF biomarkers can be used for detection during the asymptomatic stage, with changes appearing earlier than those observed in PET imaging. However, this diagnostic approach necessitates an invasive lumbar puncture, a procedure that is met with low clinical acceptance. Brain PET/MRI imaging can be used for detecting MCI and asymptomatic AD, however, changes tested by the brain PET/MRI imaging occurred later than those observed in the CSF biomarkers. Additionally, such imaging techniques are costly, and the availability of detection devices is low, with only a few hospitals in China capable of performing such detections. Furthermore, during brain PET/MRI imaging, the injection of contrast agents is required, which involves radiation, leading to relatively low patient acceptance.

Compared with detections of CSF and brain PET/MRI imaging and other biomarkers, BBBM detection has the advantages of being minimally invasive, low in cost, easy to operate and popularize and the like. Compared with CSF and PET imaging, the blood detection method is characterized by lower cost, expedited detection, and more simplified operation, and merely requires the collection of venous blood. It is non-invasive, free of radiation risks, and appli-cable to a broader population, thus providing significant guidance for the early detection and prevention of AD.

The BBBMs are used for the early detection of AD, as indicated by an important tool in an AD referral path, such that diagnosis and treatment time can be shortened. That is, BBBM (+) would further aid in cognitive function evaluation and pathological diagnosis of AD (CSF examination and PET imaging), while BBBM (−) would contribute to the pathological diagnosis of AD, eliminate other examinations of etiology leading to cognitive decline, and avoid unnecessary CSF and PET imaging examinations.

SCD refers to a condition where patients perceive a decline in memory or cognitive function over their previous normal states, while objective neuropsychological tests remain within the normal range. SCD is a stage between normal cognitive aging and MCI. SCD is caused by a number of reasons, including preclinical AD, depression, anxiety, personality disorders, sleep disorders, and the like.

SCD is quite common in the elderly population, and population-based investigations have shown that 50% to 80% of elderly with normal cognition over 65 years old reported a decline in self-consciousness. However, there is not a high clinical interest in SCD. Factors such as cognitive decline forms, characteristics of individual personality, cultural backgrounds, and false positives in statistics would lead to great difficulty in the classification and quantification of SCD. Since SCD is a subjective cognitive perception lacking objective judgment criteria, investigators have proposed additional self-rating scales specific to SCD. Currently, common scales include subjective cognitive decline questionnaires (SCD-Qs), measurement of everyday cognition (Ecog), and the like.

Many clinical epidemiological investigations have shown that individuals with SCD are at an elevated risk of progressing to AD compared to those without SCD, and meanwhile, not all patients with SCD will progress to the stage of AD or dementia.

MCI is a heterogeneous clinical syndrome characterized by mild cognitive deficits that have no significant impact on daily life. It represents a transitional stage between normal aging and mild dementia. MCI can be either caused by neurodegenerative diseases such as AD, Parkinson's disease, and frontotemporal lobar degeneration, or by other systemic, neuro-systemic and psychiatric diseases. If targeted treatment can be administered based on the etiology of MCI, it is expected to reverse the cognitive impairment or prevent its further progression.

Therefore, if AD can be screened from the preclinical stage to SCD and MCI stages, and can be effectively distinguished from other types of dementia, it would enable early intervention and targeted treatment to be available, thus preventing further disease progression.

SUMMARY

The present disclosure aims to provide a protein antigen combination for early detection of AD and application thereof.

In order to fulfill the objective of the present disclosure, the technical solution adopted in the present disclosure is as follows: An antigen combination is provided, wherein the antigen combination at least simultaneously includes any two of the following proteins: DOC2A, LGALS1, KDM4D, and ADARB1.

Preferably, an amino acid sequence of the DOC2A protein is shown in SEQ ID NO: 1, and/or an amino acid sequence of the LGALS1 protein is shown in SEQ ID NO: 2, and/or an amino acid sequence of the KDM4D protein is shown in SEQ ID NO:7, and/or an amino acid sequence of the ADARB1 protein is shown in SEQ ID NO: 9.

Preferably, the antigen combination further includes an SERF2 protein.

Preferably, an amino acid sequence of the SERF2 protein is shown in SEQ ID NO: 6.

Preferably, the antigen combination further includes any one or more of the following proteins: HIST1H2BD, ICAM1, RIOK2, and DNAJC8.

Preferably, an amino acid sequence of the HIST1H2BD protein is shown in SEQ ID NO: 3, and/or an amino acid sequence of the ICAM1 protein is shown in SEQ ID NO: 4, and/or an amino acid sequence of the RIOK2 protein is shown in SEQ ID NO:5, and/or an amino acid sequence of the DNAJC8 protein is shown in SEQ ID NO: 8.

Accordingly, the antigen combination can be applied in preparation of products for detecting/identifying AD.

Preferably, the antigen combination can be applied in preparation of products for detecting/identifying AD at a middle stage or earlier, and particularly, has outstanding advantages in preparation of products for detecting/identifying AD at an early stage or earlier.

Accordingly, reagents or kits for detecting/identifying AD are prepared by using the antigen combination.

Accordingly, the LGALS1 protein and/or the HIST1H2BD protein and/or the RIOK2 protein can be applied in preparation of products for detecting/identifying AD, wherein the amino acid sequence of the LGALS1 protein is shown in SEQ ID NO: 2, and/or the amino acid sequence of the HIST1H2BD protein is shown in SEQ ID NO:3, and/or the amino acid sequence of the RIOK2 protein is shown in SEQ ID NO: 5.

Accordingly, products, such as the reagents or the kits, for detecting/identifying AD are prepared using the proteins. The antigen combination has outstanding advantages in preparation of products for detecting/identifying AD at the middle stage or earlier, and particularly, the early stage or earlier.

The present disclosure has the following beneficial effects:

The present disclosure provides several protein antigens for effectively differentiating AD through autoantibody detection from the preclinical stage to the subjective cognitive decline (SCD) and mild cognitive impairment (MCI) stages. The detection method is simple and convenient and free from radiation, and does not cause trauma that is difficult for subjects to accept. Detection results demonstrate a high degree of consistency with those obtained through detection by CSF or "golden standard". The protein antigens involved herein can be prepared by artificial synthesis, gene recombination and other methods.

The protein antigens or the combination thereof according to the present disclosure can be used to test biological samples obtained from the subjects for the presence or levels of autoantibodies against the antigen combination, thus determining whether the subjects are at the early stage of AD or at risk of developing AD, and meanwhile, facilitate the identification of whether the type of dementia affecting the subjects is AD. Wherein the biological samples may be serum, plasma, whole blood, saliva, an oral mucosal swab, urine, lymph fluid, cerebrospinal fluid, and the like. Depending on specific conditions, the biological samples can be pretreated through methods such as extraction, dilution, and enrichment. The methods are versatile, simple, and easy to implement. When the protein antigens and the combination thereof according to the present disclosure are applied in the above tests, the presence or levels of the autoantibodies are tested by allowing the proteins or fragments thereof in the protein antigens and the combination thereof to bind to or interact with the corresponding autoantibodies, if present.

The protein antigens or the combination thereof according to the present disclosure can also be used for preparing AD-associated autoantibody early-screening reagents or AD-associated early-screening diagnostic reagents. It should be understood that the protein antigen combination can also be used to prepare kits for early-screening of AD-associated autoantibodies, and the kit can be prepared by referring to the method and the reagents for detecting the early-screening AD-associated autoantibodies by using the protein antigen combination in the examples of the present disclosure, with corresponding adjustments made as needed. The protein antigens or the combination thereof according to the present disclosure can be used for the early screening of AD and also exhibits excellent performance in the identification of AD at the early and middle stages.

In summary, the present disclosure provides several new protein antigens and the combination thereof, which can be used for early-screening detection or diagnosis of AD, and are particularly suitable for risk evaluation and prediction prior to the onset of AD. Meanwhile, the protein antigens and the combination thereof can distinguish AD from other types of dementia, and can be further prepared into the related reagents or kits according to needs.

DETAILED DESCRIPTION OF THE EMBODIMENTS

The present disclosure discovers that DOC2A, LGALS1, HIST1H2BD, ICAM1, RIOK2, SERF2, DNAJC8, KDM4D (also known as JMJD 2D) and ADARB1 proteins are closely related to the extremely early diagnosis of AD for the first time, and particularly, three proteins: LGALS1, HIST1H2BD, and RIOK2, are found to be related to the diagnosis of AD for the first time. An amino acid sequence of the DOC2A protein is shown in SEQ ID NO: 1. An amino acid sequence of the LGALS1 protein is shown in SEQ ID NO: 2. An amino acid sequence of the HIST1H2BD protein is shown in SEQ ID NO: 3. An amino acid sequence of the ICAM1 protein is shown in SEQ ID NO: 4. An amino acid sequence of the RIOK2 protein is shown in SEQ ID NO: 5. An amino acid sequence of the SERF2 protein is shown in SEQ ID NO: 6. An amino acid sequence of the KDM4D protein is shown in SEQ ID NO: 7. An amino acid sequence of the DNAJC8 protein is shown in SEQ ID NO: 8. An amino acid sequence of the ADARB1 protein is shown in SEQ ID NO: 9.

Based on the new findings, the present disclosure provides application of the proteins in preparation of related products (such as kits) for detecting and diagnosing AD. The proteins may be used alone or in combination to form a protein composition.

The technical solutions in the examples of the present disclosure will be clearly and completely described below, and apparently, the described examples are merely part, rather than all of the examples of the present disclosure. Unless otherwise specified, technical means used in the examples are conventional means that are well-known to a person skilled in the art. The data obtained is average values obtained after at least three repetitions, and the data obtained from each repetition is valid data.

Example 1: Construction, Expression and Purification of Recombinant Vector of Protein Antigen A method for obtaining a protein antigen is as follows: coding DNA of the protein antigen was synthesized, primers were designed by taking the synthetic DNA as a template, a gene fragment of the protein antigen or a fragment thereof was cloned into an expression plasmid through polymerase chain reaction (PCR), enzyme digestion, ligation and other molecular cloning methods, the gene fragment in the expression plasmid was then expressed by means of *Escherichia coli* (*E. coli*), yeast or cells, and finally, a target protein was obtained through chromatographic purification. Meanwhile, Trx, GST, AVI, HIS, and c-myc tags could also be selectively added to the protein antigen or the fragment thereof. The addition of these tags could facilitate the purification or labeling of the protein antigen without substantially altering the binding properties of the antigen to autoantibodies thereof.

DOC2A, LGALS1, HIST1H2BD, ICAM1, RIOK2, SERF2, DNAJC8, KDM4D and ADARB1 proteins were selected, and respective database IDs of the above proteins are specifically shown in Table 1.

TABLE 1

| Comparison table of database ID of each candidate protein | | |
| --- | --- | --- |
| Protein name | Database ID (uniprot) | Sequence |
| DOC2A | Q14183 | SEQ ID NO: 1 |
| LGALS1 | P09382 | SEQ ID NO: 2 |
| HIST1H2BD | P58876 | SEQ ID NO: 3 |
| ICAM1 | P05362 | SEQ ID NO: 4 |
| RIOK2 | Q9BVS4 | SEQ ID NO: 5 |
| SERF2 | P84101-3 | SEQ ID NO: 6 |
| KDM4D | Q6B0I6 | SEQ ID NO: 7 |
| DNAJC8 | O75937 | SEQ ID NO: 8 |
| ADARB1 | P78563 | SEQ ID NO: 9 |

Using a human cDNA library (purchased from Invitrogen Company) or whole gene synthetic DNA as a template, primers were designed respectively, and a gene fragment of the protein was cloned into a pET28 plasmid through PCR, enzyme digestion, ligation and other molecular cloning methods. Meanwhile, HIS, FLAG and other tags were added to an N-terminal of the protein to form a fusion protein. A recombinant expression vector was identified by DNA sequencing and confirmed to contain the correct protein gene fragment. It should be noted that the added tag(s) is merely convenient for identification and extraction of the protein, and does not have a decisive impact on the function of the protein as the antigen. When in use, the tag may not be added necessarily, or other tags may be added as needed, or alternative labeling/identification methods may be employed.

The recombinant plasmid containing the protein gene fragment was transformed into competent cells of *E. coli* BL21 (DE3), and the clones were selected and inoculated into LB media, and then shaking-cultured at 37° C. When the *E. coli* BL21 (DE3) density $OD_{600}$ reached approximately 0.8, temperature was reduced to 16° C., and 0.1 mM isopropylthio-beta-D-galactoside (IPTG) was added to each LB medium to induce expression overnight, and bacterial cells were obtained.

The expression-induced bacterial cells were collected by centrifugation and rinsed twice with phosphate buffer saline (PBS). The bacterial cells were resuspended and dispersed in a lysis buffer (5-10 mL of lysis buffer per gram of bacterial cells), and were then subjected to ultrasonic disruption (ultrasound power: 200 W, ultrasonication for 5 seconds with a 5-second interval) under an ice bath. After cell disruption, the bacterial cells were centrifuged at 13000 rpm and at 10° C. for 20 minutes, and a supernatant was collected, and then purified via two steps: Ni column affinity chromatography and molecular sieve chromatography. The purified target protein was analyzed by sodium dodecyl sulfate polyacrylamide gel electrophoresis (SDS-PAGE) to confirm the molecular weight and purity of the protein, and after the concentration of the protein was determined via a Bradford method, the protein was stored at −80° C. for later use. The purified candidate proteins were obtained.

Example 2: Display of Effect of Each Candidate Protein Alone in Detection of AD-Derived SCD and AD-Derived MCI Samples 1. Solutions and reagents used in this example were as follows:
 (1) A coating buffer was a PBS buffer (pH=7.4). A preparation method is as follows: 3.58 g of $Na_2HPO_4 \cdot 12H_2O$, 0.23 g of $KH_2PO_4 \cdot 2H_2O$, 0.2 g of KCl and 8.0 g of NaCl were accurately weighed and dissolved in water, and then diluted with the water to 1 L.
 (2) Blocking buffer/sample diluent/antibody diluent: 10 g of BSA (bovine serum albumin) was dissolved in 800 mL of coating buffer, and diluted with the coating buffer to 1 L.
 (3) Washing buffer: A washing buffer should be prepared when using. 0.5% Tween 20 (V/V) was added to the coating buffer before use, and pH is 7.4.
 (4) A TMB chromogenic agent was purchased from KPL Company.
 (5) Stopping solution: 1M hydrochloric acid.
2. A solid phase was coated with the protein. Each purified candidate protein obtained in Example 1 was diluted to a concentration of 5 μg/mL using the coating buffer, and the diluted protein was then added to a 96-well plate at 50 μL/well and coated overnight at 4° C. for incubation. On the following day, the solution was discarded, and the plate was dried, and washed with the washing buffer three times, with each well receiving 200 μL per time. 200 μL of blocking buffer was added for incubation at room temperature for 1 hour, and then the plate was dried after the blocking buffer was discarded, washed with the washing buffer three times, with each well receiving 200 μL per time, and dried again. The solid phase-coated protein antigen in the 96-well plate was obtained.
3. The sample to be tested was added. Human serum to be tested was diluted by a factor of 100 with the sample diluent and then added to the 96-well plate containing the protein to be tested, and 50 μL of the diluted sample to be tested was added to each well. The 96-well plate was then placed on a microplate shaker, where it was incubated at room temperature for 1 hour; and the plate was dried, washed with the washing buffer three times, with each well receiving 200 μL per time, and then dried again.
4. An enzyme-labeled second antibody was added. 1.0 mg/mL horseradish peroxidase-labeled recombinant goat anti-human immunoglobulin G antibody (purchased from Jackson ImmunoResearch Inc.) was diluted by a factor of 20000 with the antibody diluent, and then added to the 96-well plate treated in step 3 at 50 μL/well. The 96-well plate was then placed on a microplate shaker, where it was incubated at room temperature for 0.5 hour; and the plate was dried, washed with the washing buffer three times, with each well receiving 200 μL per time, and then dried again.

5. Color reaction and optical density reading. In the 96-well plate treated in step 4, a TMB chromogenic agent was added to the plate at 50 μL/well, followed by shaking for 15 seconds. The reaction was kept away from light for 15 minutes at room temperature, and then 50 μL of stopping solution was added. Then an absorbance value at 450 nm was read by a microplate reader to obtain a detection signal (S) of each sample to be tested.

6. Analysis of sensitivity and specificity. 300 positive samples (identified as positive samples for enrollment) and 300 negative samples (serum from healthy subjects) were collected, respectively.

The inclusion criteria for defining the positive samples are as follows: subjects simultaneously meet the following conditions: subjective sensory memory decline rather than other cognitive impairment diseases, onset duration of less than 5 years, age at onset greater than 55 years, concern about cognitive deterioration, and self-sensory memory being inferior compared to peers of the same age. No recent (within the past 7 days) or long-term (≥5 years) administration of the following drugs does not happen, including immunomodulators, antidepressants or neuroleptics containing anticholinergic ingredients, anti-Parkinsonian drugs, or other clinical trial drugs; and no history of autoimmune diseases, primarily including rheumatoid arthritis, hyperthyroidism, systemic lupus erythematosus, primary biliary cirrhosis, and the like. Scale evaluation: Global Deterioration Scale (GDs) scores of 2-3, Clinical Dementia Rating Scale (CDR) score≤0.5, memory score below 1.5 standard deviations from the age- and education-matched control group, Mini-Mental State Examination (MMsE) scores>24, and mattis Dementia Rating Scale (DRs) score>123.

It should be noted that the existing universal diagnosis methods of AD are not completely accurate, and particularly, are difficult in precisely diagnosing patients with extremely early (potential) AD. Therefore, samples, as identified as positive herein, do not necessarily represent all true cases of (extremely early) AD, where there may be normal individuals who have been misdiagnosed or misjudged, as well as individuals with cognitive decline, cognitive impairment, or deterioration of memory caused by conditions other than AD.

The inclusion criteria for defining negative samples (healthy individuals) are as follows: subjects simultaneously meet the following conditions: (1) subjects are conscious and stable in vital signs, and have no abnormal neurological symptoms or signs, and no history of nervous system diseases and mental system diseases: (2) no subjective memory function decline or history of other neurological or psychiatric disorders, and no insomnia or chronic insomnia recently (insomnia symptoms occurring ≥3 times per week and persisting for ≥3 months): (3) Mini-Mental State Examination (MMSE) score >26: (4) Montreal Cognitive Assessment (MoCA) score >26: (5) Hamilton Depression Scale (HAMD) score <7: (6) Hamilton Anxiety Scale (HAMA) (14 items) score <7: (7) Clinical Dementia Rating (CDR) score of 0: (8) no recent (within the past 7 days) or long-term (≥5 years) administration of the following drugs, including the immunomodulators, the antidepressants or neuroleptics containing anticholinergic ingredients, the anti-Parkinsonian drugs, or other clinical trial drugs; and (9) no history of autoimmune diseases, primarily including rheumatoid arthritis, hyperthyroidism, systemic lupus erythematosus, primary biliary cirrhosis, and the like.

A detection signal (S) of each sample was determined according to the method (absorption value at 450 nm wavelength) in step 4. The negative samples were taken as negative reference samples. The mean (M, average value) and standard deviation (SD) of detection signals(S) of all negative reference samples were calculated, and M+3 SD was taken as a cut-off value.

The samples (S≥M+3 SD) with the detection signal (S)≥ cut off value were regarded as positive; and the samples (S<M+3 SD) with the detection signal (S)<cut off value were regarded as negative.

The specificity and sensitivity were calculated based on the positive and negative results of the samples. Wherein, specificity refers to the proportion of healthy subjects whose samples are correctly determined as negative, that is, the number of the negative samples which are correctly determined as negative divided by the total number of the negative samples. Sensitivity refers to the proportion of positive samples of enrolled patients that are determined as positive, that is, the number of the positive samples which are correctly determined as positive divided by the total number of the positive samples. The sensitivity and specificity of each protein to be tested as an antigen for sample detection are obtained through calculation.

Meanwhile, the positive samples were respectively detected in hospitals through the following methods: beta-Amyloid Accumulation (CSF/PET), FDG-PET/fMRI or Tau-mediated neuronal injury (CSF). The sensitivity was calculated using the detection results from the hospitals as a control. Additionally, due to the presence of radiation and/or invasive procedures associated with tests such as beta-Amyloid Accumulation and the like, normal individuals (negative samples) did not perform the corresponding detection, resulting in the absence of specificity data for these cases. The results are shown in Table 2.

TABLE 2

Comparison table of detection result of each candidate protein

| Candidate protein/detection method | Specificity | | Sensitivity | |
|---|---|---|---|---|
| | The number of samples detected as negative | Ratio | The number of samples detected as positive | Ratio |
| LGALS1 | 294 | 98% | 66 | 22% |
| HIST1H2BD | 285 | 95% | 57 | 19% |
| RIOK2 | 288 | 96% | 72 | 24% |
| KDM4D | 285 | 95% | 81 | 27% |
| SERF2 | 288 | 96% | 93 | 31% |
| ADARB1 | 282 | 94% | 99 | 33% |
| ICAM1 | 282 | 94% | 66 | 22% |
| DOC2A | 282 | 94% | 72 | 24% |
| DNAJC8 | 294 | 98% | 60 | 20% |
| β-Amyloid Accumulation | \ | \ | 117 | 39% |
| FDG-PET/fMRI | \ | \ | 72 | 24% |
| Tau-mediated neuronal injury | \ | \ | 54 | 18% |

Results indicate that the existing commonly used convenient methods (self-evaluation and scale evaluation) had low accuracy in detecting the extremely early AD, and samples as identified as positive contained a significant proportion of misdiagnosed patients.

Example 3: Display of Effect of Protein
Compositions in Combined Detection of
AD-Derived SCD and AD-Derived MCI Samples 1. Antigen compositions are used for detection based on
   a "single-index" method.

The "single-index" method refers to an approach where
detection is based on each antigen, that is, one antigen
corresponding to a piece of data. When a certain sample to
be tested is detected using a certain antigen combination, the
result for the detection of the sample based on the antigen
combination is regarded as positive if any antigen from the
antigen combination yields a positive detection signal; and
otherwise, the result is regarded as negative.

Different antigen combinations are formed by using can-
didate protein antigens in Example 2, as specifically shown
in Table 3. The antigen combinations were used to detect the
specificity and sensitivity of the positive and negative
samples from Example 1 with reference to the method as
described in Example 2. The detection results are shown in
Table 4. It should be noted that the inventor did not limit
experiments to the combinations as shown in Table 3: rather,
the inventor obtained the antigen combinations shown in
Table 3 after a large number of preliminary tests.

TABLE 3

Comparison table of each antigen combination

| Combination | Candidate protein antigens contained in combination |
|---|---|
| Combination 1 | SERF2, LGALS1, KDM4D |
| Combination 2 | SERF2, DOC2A, ADARB1 |
| Combination 3 | SERF2, HIST1H2BD, RIOK2 |
| Combination 4 | SERF2, DNAJC8, ADARB1 |
| Combination 5 | LGALS1, KDM4D, ADARB1 |
| Combination 6 | SERF2, LGALS1, KDM4D, ADARB1 |
| Combination 7 | DOC2A, LGALS1, KDM4D, ADARB1 |
| Combination 8 | SERF2, LGALS1, KDM4D, ADARB1, DOC2A |
| Combination 9 | SERF2, DOC2A, LGALS1, HIST1H2BD, ICAM1, RIOK2, ADARB1, KDM4D, DNAJC8 |

TABLE 4

Comparison table of detection result of each antigen combination
based on "single-index" method

| Combination | Sensitivity | | Specificity | |
|---|---|---|---|---|
| | The number of samples detected as positive | Ratio | The number of samples detected as negative | Ratio |
| Combination 1 | 171 | 57% | 267 | 89% |
| Combination 2 | 198 | 66% | 255 | 85% |
| Combination 3 | 159 | 53% | 261 | 87% |
| Combination 4 | 192 | 64% | 267 | 89% |
| Combination 5 | 171 | 57% | 264 | 88% |
| Combination 6 | 207 | 69% | 255 | 85% |
| Combination 7 | 201 | 67% | 246 | 82% |
| Combination 8 | 225 | 75% | 237 | 79% |
| Combination 9 | 231 | 77% | 198 | 66% |
| β-Amyloid Accumulation | 117 | 39% | \ | \ |
| FDG-PET/fMRI | 72 | 24% | \ | \ |
| Tau-mediated neuronal injury | 54 | 18% | \ | \ |

Results indicate that in an event of judgment based on the
"single-index" method, sensitivity was higher compared to
three commonly used existing methods. However, specific-
ity was relatively lower compared to the detection based on individual protein antigens, suggesting that the detection
accuracy could be further improved.

2. Antigen compositions are used for detection based on
   a "double-index" method.

The "double-index" method refers to an approach where
when a certain sample to be tested is detected using a certain
antigen combination, the detection result of the sample is
regarded as positive if two or more antigens from the antigen
combination yield positive detection signals; and otherwise,
the result is regarded as negative. The rest of operations are
the same as the "single-index" method. Meanwhile, in an
event of the detection based on multiple existing detection
methods, the "double-index" method is also employed for
judgment, that is, the detection result is identified as positive
only if both detection methods yield positive results simul-
taneously; and otherwise, the result is regarded as negative.
For example, in an event of the combination of beta-
Amyloid Accumulation+FDG-PET/fMRI (CSF/PET), only
when the results from detections of both beta-Amyloid
Accumulation and FDG-PET/fMRI (CSF/PET) are positive
can the detection result be regarded as positive. The results
are shown in Table 5.

TABLE 5

Comparison table of detection result of each antigen combination
based on "double-index" method

| Combination | Sensitivity | | Specificity | |
|---|---|---|---|---|
| | The number of samples detected as positive | Ratio | The number of samples detected as negative | Ratio |
| Combination 1 | 60 | 20% | 300 | 100% |
| Combination 2 | 60 | 20% | 297 | 99% |
| Combination 3 | 57 | 19% | 300 | 100% |
| Combination 4 | 57 | 19% | 300 | 100% |
| Combination 5 | 66 | 22% | 297 | 99% |
| Combination 6 | 93 | 31% | 294 | 98% |
| Combination 7 | 102 | 34% | 297 | 99% |
| Combination 8 | 135 | 45% | 294 | 98% |
| Combination 9 | 177 | 59% | 282 | 94% |
| β-Amyloid Accumulation | 117 | 39% | \ | \ |
| FDG-PET/fMRI (CSF/PET) | 72 | 24% | \ | \ |
| Tau-mediated neuronal injury(CSF) | 54 | 18% | \ | \ |
| β-Amyloid Accumulation + FDG-PET/fMRI (CSF/PET) | 72 | 24% | \ | \ |
| β-Amyloid Accumulation + Tau-mediated neuronal injury(CSF) | 42 | 14% | \ | \ |
| FDG-PET/fMRI + Tau-mediated neuronal injury(CSF) | 33 | 11% | | |

Results indicate that the detection result of the "double-
index" method was closer to the detection results of beta-
Amyloid Accumulation and the like, and the specificity was
obviously higher, suggesting that the detection accuracy of
the "double-index" method was higher.

3. Samples identified as positive by detection of beta-
   Amyloid and the like were detected by using each
   individual protein antigen or by using antigen compo-
   sitions based on the "single-index" method or "double-
   index" method.

To further confirm the overlap between the positive results detected by the individual antigens or each antigen combination and the positive results detected by the existing methods, the samples identified as positive through the following methods in Table 5: beta-Amyloid Accumulation, FDG-PET/fMRI (CSF/PET), Tau-mediated neuronal injury (CSF), beta-Amyloid Accumulation+FDG-PET/fMRI (CSF/PET),beta-Amyloid Accumulation+Tau-mediated neuronal injury (CSF), and FDG-PET/fMRI+Tau-mediated neuronal injury (CSF), were detected again by using each antigen combination. The results are shown in Table 6. The total number of the samples identified as positive in Table 6 corresponds to the number of the samples identified as positive through detection by each existing method in Table 5.

to have higher accuracy, and patients who were regarded as positive through detection by the existing methods could be detected completely and accurately.

Example 4: Display of Effect of Protein Compositions in Combined Detection of Patients with Early AD and Middle AD 100 clinical samples were taken as positive samples with early AD, 100 clinical samples were taken as positive samples with middle AD, and a detection signal (S) of each sample was determined using the candidate antigens and combinations thereof as shown in Table 3 based on the method in Example 2. The samples (S≥M+3 SD) with the

TABLE 6

Comparison table of detection result of each antigen or antigen combination

| Antigen or antigen Combination | β-Amyloid Accumulation (CSF/PET) Total number 117 | FDG-PET/fMRI Total number 72 | Tau-mediated neuronal injury (CSF) Total number 54 | β-Amyloid Accumulation + FDG-PET/fM (CSF/PET) Total number 72 | β-Amyloid Accumulation + Tau-mediated neuronal injury (CSF) Total number 42 | FDG-PET/fMRI + Tau-mediated neuronal injury (CSF) Total number 33 |
|---|---|---|---|---|---|---|
| LGALS1 | 48 | 36 | 36 | 36 | 30 | 21 |
| HIST1H2BD | 48 | 36 | 33 | 36 | 30 | 24 |
| RIOK2 | 57 | 45 | 18 | 45 | 18 | 18 |
| KDM4D | 60 | 45 | 18 | 45 | 18 | 18 |
| SERF2 | 63 | 33 | 24 | 33 | 21 | 18 |
| ADARB1 | 66 | 42 | 33 | 42 | 27 | 18 |
| ICAM1 | 60 | 36 | 27 | 36 | 27 | 18 |
| DOC2A | 42 | 30 | 18 | 30 | 12 | 12 |
| DNAJC8 | 36 | 21 | 15 | 21 | 9 | 9 |
| Single-index combination 1 | 111 | 69 | 48 | 69 | 42 | 33 |
| Single index Combination 2 | 114 | 69 | 54 | 69 | 42 | 33 |
| Single-index combination 3 | 111 | 69 | 45 | 69 | 42 | 33 |
| Single-index combination 4 | 108 | 63 | 54 | 63 | 42 | 33 |
| Single-index combination 5 | 102 | 66 | 48 | 66 | 39 | 30 |
| Single-index combination 6 | 117 | 72 | 51 | 72 | 42 | 33 |
| Single-index combination 7 | 117 | 72 | 54 | 72 | 42 | 33 |
| Single-index combination 8 | 117 | 72 | 54 | 72 | 42 | 33 |
| Single-index combination 9 | 117 | 72 | 54 | 72 | 42 | 33 |
| Double-index combination 1 | 51 | 36 | 24 | 36 | 21 | 18 |
| Double-index combination 2 | 51 | 30 | 18 | 30 | 15 | 12 |
| Double-index combination 3 | 51 | 39 | 24 | 39 | 21 | 21 |
| Double-index combination 4 | 54 | 30 | 18 | 30 | 15 | 12 |
| Double-index combination 5 | 63 | 48 | 36 | 48 | 33 | 24 |
| Double-index combination 6 | 81 | 54 | 45 | 54 | 39 | 30 |
| Double-index combination 7 | 117 | 72 | 54 | 72 | 42 | 33 |
| Double-index combination 8 | 117 | 72 | 54 | 72 | 42 | 33 |
| Double-index combination 9 | 117 | 72 | 54 | 72 | 42 | 33 |

Results indicate that the detection results of the combinations 7, 8 and 9 had a high matching degree with those from the existing detection methods which were recognized detection signal (S)≥cut off value were regarded as positive; and the samples (S<M+3 SD) with the detection signal (S)<cut off value were regarded as negative.

The specificity and sensitivity were calculated based on the positive and negative results of the samples. Wherein, specificity refers to the proportion of healthy subjects whose samples are correctly determined as negative, that is, the number of the negative samples which are correctly determined as negative divided by the total number of the negative samples. Sensitivity refers to the proportion of positive samples of enrolled patients that are determined as positive, that is, the number of the positive samples which are correctly determined as positive divided by the total number of the positive samples. The sensitivity and specificity of each protein to be tested as an antigen for sample detection are obtained through calculation. The results are shown in Table 7.

TABLE 7

Comparison table of detection result of each antigen or antigen combination

| Antigen or antigen Combination | Early sensitivity | Medium sensitivity | Medium and early sensitivity | Specificity |
|---|---|---|---|---|
| LGALS1 | 46% | 28% | 37% | 98% |
| HIST1H2BD | 36% | 24% | 30% | 95% |
| RIOK2 | 28% | 20% | 24% | 96% |
| KDM4D | 44% | 24% | 34% | 95% |
| SERF2 | 34% | 28% | 31% | 96% |
| ADARB1 | 42% | 38% | 40% | 94% |
| ICAM1 | 20% | 16% | 18% | 94% |
| DOC2A | 18% | 10% | 14% | 94% |
| DNAJC8 | 36% | 34% | 35% | 98% |
| Single-index combination 1 | 68% | 62% | 65% | 89% |
| Single-index combination 2 | 68% | 62% | 65% | 85% |
| Single-index combination 3 | 70% | 54% | 62% | 87% |
| Single-index combination 4 | 74% | 72% | 73% | 89% |
| Single-index combination 5 | 72% | 64% | 68% | 88% |
| Single-index combination 6 | 74% | 76% | 75% | 85% |

TABLE 7-continued

Comparison table of detection result of each antigen or antigen combination

| Antigen or antigen Combination | Early sensitivity | Medium sensitivity | Medium and early sensitivity | Specificity |
|---|---|---|---|---|
| Single-index combination 7 | 80% | 66% | 73% | 82% |
| Single-index combination 8 | 80% | 78% | 79% | 79% |
| Single-index combination 9 | 94% | 86% | 90% | 66% |
| Double-index combination 1 | 36% | 18% | 27% | 100% |
| Double-index combination 2 | 24% | 14% | 19% | 99% |
| Double-index combination 3 | 24% | 18% | 21% | 100% |
| Double-index combination 4 | 32% | 26% | 29% | 100% |
| Double-index combination 5 | 46% | 22% | 34% | 99% |
| Double-index combination 6 | 52% | 34% | 43% | 98% |
| Double-index combination 7 | 50% | 30% | 40% | 99% |
| Double-index combination 8 | 58% | 42% | 50% | 98% |
| Double-index combination 9 | 78% | 66% | 72% | 94% |

Results indicate that the detection results of the combinations 5, 6, 7, 8, and 9 had higher specificity and better sensitivity at early and middle stages of AD.

The above-described examples are merely the description of preferred implementations of the present disclosure, and do not limit the scope of the present disclosure. Various modifications, variations, alterations, and substitutions made by those of ordinary skill in the art to the technical solutions of the present disclosure are intended to fall within the scope of protection identified by the claims of the present disclosure without departing from the design spirit of the present disclosure.

What is claimed is:

1. An antigen combination for diagnosis of early Alzheimer's disease, wherein the antigen combination comprises: (a) small EDRK-rich factor 2 (SERF2), galectin-1 (LGALS1), lysine-specific demethylase 4D (KDM4D), and adenosine deaminase RNA-specific B1 (ADARB1), wherein at least one of SERF2, LGALS1, KDM4D, and ADARB1 is labeled with a tag for purification or identification; or (b) double C2-like domain-containing protein alpha (DOC2A), LGALS1, KDM4D, and ADARB1, wherein at least one of DOC2A, LGALS1, KDM4D, and ADARB1 is labeled with a tag for purification or detection; wherein SERF2 comprises the amino acid sequence set forth in SEQ ID NO: 6, LGALS1 comprises the amino acid sequence set forth in SEQ ID NO: 2, KDM4D comprises the amino acid sequence set forth in SEQ ID NO: 7, ADARB1 comprises the amino acid sequence set forth in SEQ ID NO: 9, DOC2A comprises the amino acid sequence set forth in SEQ ID NO: 1.

2. The antigen combination according to claim 1, wherein the antigen combination comprises SERF2, LGALS1, KDM4D, ADARB1, and DOC2A.

3. The antigen combination according to claim 2, wherein the antigen combination further comprises histone cluster 1 H2B family member D (HIST1H2BD), intercellular adhesion molecule 1 (ICAM1), RIO kinase 2 (RIOK2), and DNAJ heat shock protein family (Hsp40) member C8 (DNAJC8), wherein HIST1H2BD comprises the amino acid sequence set forth in SEQ ID NO: 3, ICAM1 comprises the amino acid sequence set forth in SEQ ID NO: 4, RIOK2 comprises the amino acid sequence set forth in SEQ ID NO: 5, and DNAJC8 comprises the amino acid sequence set forth in SEQ ID NO: 8.

4. A reagent or kit for diagnosing/detecting early Alzheimer's disease, comprising the antigen combination according to claim 1.

* * * * *

SEQUENCE LISTING

```
Sequence total quantity: 9
SEQ ID NO: 1            moltype = AA  length = 400
FEATURE                 Location/Qualifiers
source                  1..400
                        mol_type = protein
                        note = DOC2A
                        organism = Homo sapiens
SEQUENCE: 1
MRGRRGDRMT INIQEHMAIN VCPGPIRPIR QISDYFPRGP GPEGGGGGGG EAPAHLVPLA  60
LAPPAALLGA TTPEDGAEVD SYDSDDATAL GTLEFDLLYD RASCTLHCSI LRAKGLKPMD  120
FNGLADPYVK LHLLPGACKA NKLKTKTQRN TLNPVWNEDL TYSGITDDDI THKVLRIAVC  180
DEDKLSHNEF IGEIRVPLRR LKPSQKKHFN ICLERQVPLA SPSSMSAALR GISCYLKELE  240
QAEQGQGLLE ERGRILLSLS YSSRRRGLLV GILRCAHLAA MDVNGYSDPY VKTYLRPDVD  300
KKSKHKTCVK KKTLNPEFNE EFFYEIELST LATKTLEVTV WDYDIGKSND FIGGVSLGPG  360
ARGEARKHWS DCLQQPDAAL ERWHTLTSEL PPAAGALSSA             400

SEQ ID NO: 2            moltype = AA  length = 135
FEATURE                 Location/Qualifiers
source                  1..135
                        mol_type = protein
                        note = LGALS1
                        organism = Homo sapiens
SEQUENCE: 2
MACGLVASNL NLKPGECLRV RGEVAPDAKS FVLNLGKDSN NLCLHFNPRF NAHGDANTIV  60
CNSKDGGAWG TEQREAVFPF QPGSVAEVCI TFDQANLTVK LPDGYEFKFP NRLNLEAINY  120
MAADGDFKIK CVAFD                                       135
```

```
SEQ ID NO: 3              moltype = AA  length = 126
FEATURE                   Location/Qualifiers
source                    1..126
                          mol_type = protein
                          note = HIST1H2BD
                          organism = Homo sapiens
SEQUENCE: 3
MPEPTKSAPA PKKGSKKAVT KAQKKDGKKR KRSRKESYSV YVYKVLKQVH PDTGISSKAM  60
GIMNSFVNDI FERIAGEASR LAHYNKRSTI TSREIQTAVR LLLPGELAKH AVSEGTKAVT  120
KYTSSK                                                            126

SEQ ID NO: 4              moltype = AA  length = 532
FEATURE                   Location/Qualifiers
source                    1..532
                          mol_type = protein
                          note = ICAM1
                          organism = Homo sapiens
SEQUENCE: 4
MAPSSPRPAL PALLVLLGAL FPGPGNAQTS VSPSKVILPR GGSVLVTCST SCDQPKLLGI  60
ETPLPKKELL LPGNNRKVYE LSNVQEDSQP MCYSNCPDGQ STAKTFLTVY WTPERVELAP  120
LPSWQPVGKN LTLRCQVEGG APRANLTVVL LRGEKELKRE PAVGEPAEVT TTVLVRRDHH  180
GANFSCRTEL DLRPQGLELF ENTSAPYQLQ TFVLPATPPQ LVSPRVLEVD TQGTVVCSLD  240
GLFPVSEAQV HLALGDQRLN PTVTYGNDSF SAKASVSVTA EDEGTQRLTC AVILGNQSQE  300
TLQTVTIYSF PAPNVILTKP EVSEGTEVTV KCEAHPRAKV TLNGVPAQPL GPRAQLLLKA  360
TPEDNGRSFS CSATLEVAGQ LIHKNQTREL RVLYGPRLDE RDCPGNWTWP ENSQQTPMCQ  420
AWGNPLPELK CLKDGTFPLP IGESVTVTRD LEGTYLCRAR STQGEVTRKV TVNVLSPRYE  480
IVIITVVAAA VIMGTAGLST YLYNRQRKIK KYRLQQAQKG TPMKPNTQAT PP          532

SEQ ID NO: 5              moltype = AA  length = 552
FEATURE                   Location/Qualifiers
source                    1..552
                          mol_type = protein
                          note = RIOK2
                          organism = Homo sapiens
SEQUENCE: 5
MGKVNVAKLR YMSRDDFRVL TAVEMGMKNH EIVPGSLIAS IASLKHGGCN KVLRELVKHK  60
LIAWERTKTV QGYRLTNAGY DYLALKTLSS RQVVESVGNQ MGVGKESDIY IVANEEGQQF  120
ALKLHRLGRT SFRNLKNKRD YHKHRHNVSW LYLSRLSAMK EFAYMKALYE RKFPVPKPID  180
YNRHAVVMEL INGYPLCQIH HVEDPASVYD EAMELIVKLA NHGLIHGDFN EFNLILDESD  240
HITMIDFPQM VSTSHPNAEW YFDRDVKCIK DFFMKRFSYE SELFPTFKDI RREDTLDVEV  300
SASGYTKEMQ ADDELLHPLG PDDKNIETKE GSEFSFSDGE VAEKAEVYGS ENESERNCLE  360
ESEGCYCRSS GDPEQIKEDS LSEESADARS FEMTEFNQAL EEIKGQVVEN NSVTEFSEEK  420
NRTENYNRQD GQRVQGGVPA GSDEYEDECP HLIALSSLNR EFRPFRDEEN VGAMNQYRTR  480
TLSITSSGSA VSCSTIPPEL VKQKVKRQLT KQQKSAVRRR LQKGEANIFT KQRRENMQNI  540
KSSLEAASFW GE                                                     552

SEQ ID NO: 6              moltype = AA  length = 61
FEATURE                   Location/Qualifiers
source                    1..61
                          mol_type = protein
                          note = SERF2
                          organism = Homo sapiens
SEQUENCE: 6
MTRGNQRELA RQKNMKKQSD SVKGKRRDDG LSAAARKQRD SEIMQQKQKK ANEKKEEPKS  60
E                                                                 61

SEQ ID NO: 7              moltype = AA  length = 523
FEATURE                   Location/Qualifiers
source                    1..523
                          mol_type = protein
                          note = KDM4D
                          organism = Homo sapiens
SEQUENCE: 7
METMKSKANC AQNPNCNIMI FHPTKEEFND FDKYIAYMES QGAHRAGLAK IIPPKEWKAR  60
ETYDNISEIL IATPLQQVAS GRAGVFTQYH KKKKAMTVGE YRHLANSKKY QTPPHQNFED  120
LERKYWKNRI YNSPIYGADI SGSLFDENTK QWNLGHLGTI QDLLEKECGV VIEGVNTPYL  180
YFGMWKTTFA WHTEDMDLYS INYLHLGEPK TWYVVPPEHG QRLERLAREL FPGSSRGCGA  240
FLRHKVALIS PTVLKENGIP FNRITQEAGE FMVTFPYGYH AGFNHGFNCA EAINFATPRW  300
IDYGKMASQC SCGEARVTFS MDAFVRILQP ERYDLWKRGQ DRAVVDHMEP RVPASQELST  360
QKEVQLPRRA ALGLRQLPSH WARHSPWPMA ARSGTRCHTL VCSSLPRRSA VSGTATQPRA  420
AAVHSSKKPS STPSSTPGPS AQIIHPSNGR RGRGRPPQKL RAQELTLQTP AKRPLLAGTT  480
CTASGPEPEP LPEDGALMDK PVPLSPGLQH PVKASGCSWA PVP                   523

SEQ ID NO: 8              moltype = AA  length = 253
FEATURE                   Location/Qualifiers
source                    1..253
                          mol_type = protein
                          note = DNAJC8
                          organism = Homo sapiens
```

-continued

```
SEQUENCE: 8
MAASGESGTS GGGGSTEEAF MTFYSEVKQI EKRDSVLTSK NQIERLTRPG SSYFNLNPFE   60
VLQIDPEVTD EEIKKRFRQL SILVHPDKNQ DDADRAQKAF EAVDKAYKLL LDQEQKKRAL  120
DVIQAGKEYV EHTVKERKKQ LKKEGKPTIV EEDDPELFKQ AVYKQTMKLF AELEIKRKER  180
EAKEMHERKR QREEEIEAQE KAKREREWQK NFEESRDGRV DSWRNFQANT KGKKEKKNRT  240
FLRPPKVKME QRE                                                    253

SEQ ID NO: 9          moltype = AA  length = 741
FEATURE               Location/Qualifiers
source                1..741
                      mol_type = protein
                      note = ADARB1
                      organism = Homo sapiens
SEQUENCE: 9
MDIEDEENMS SSSTDVKENR NLDNVSPKDG STPGPGEGSQ LSNGGGGGPG RKRPLEEGSN   60
GHSKYRLKKR RKTPGPVLPK NALMQLNEIK PGLQYTLLSQ TGPVHAPLFV MSVEVNGQVF  120
EGSGPTKKKA KLHAAEKALR SFVQFPNASE AHLAMGRTLS VNTDFTSDQA DFPDTLFNGF  180
ETPDKAEPPF YVGSNGDDSF SSSGDLSLSA SPVPASLAQP PLPVLPPFPP PSGKNPVMIL  240
NELRPGLKYD FLSESGESHA KSFVMSVVVD GQFFEGSGRN KKLAKARAAQ SALAAIFNLH  300
LDQTPSRQPI PSEGLQLHLP QVLADAVSRL VLGKFGDLTD NFSSPHARRK VLAGVVMTTG  360
TDVKDAKVIS VSTGTKCING EYMSDRGLAL NDCHAEIISR RSLLRFLYTQ LELYLNNKDD  420
QKRSIFQKSE RGGFRLKENV QFHLYISTSP CGDARIFSPH EPILEGSRSY TQAGVQWCNH  480
GSLQPRPPGL LSDPSTSTFQ GAGTTEPADR HPNRKARGQL RTKIESGEGT IPVRSNASIQ  540
TWDGVLQGER LLTMSCSDKI ARWNVVGIQG SLLSIFVEPI YFSSIILGSL YHGDHLSRAM  600
YQRISNIEDL PPLYTLNKPL LSGISNAEAR QPGKAPNFSV NWTVGDSAIE VINATTGKDE  660
LGRASRLCKH ALYCRWMRVH GKVPSHLLRS KITKPNVYHE SKLAAKEYQA AKARLFTAFI  720
KAGLGAWVEK PTEQDQFSLT P                                           741
```